US011343904B1

(12) United States Patent
Sultana (10) Patent No.: US 11,343,904 B1
(45) Date of Patent: May 24, 2022

(54) MULTI-FUNCTIONAL NANOMATERIAL SENSOR PLATFORM

(71) Applicant: United States of America as represented by the Administrator of NASA, Washington, DC (US)

(72) Inventor: Mahmooda Sultana, Laurel, MD (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 0 days.

(21) Appl. No.: 17/181,102

(22) Filed: Feb. 22, 2021

Related U.S. Application Data (60) Provisional application No. 63/035,987, filed on Jun. 8, 2020.

(51) Int. Cl.
| | | |
|---|---|---|
| *H05K 1/02* | (2006.01) | |
| *H05K 3/12* | (2006.01) | |
| *B29C 64/112* | (2017.01) | |
| *G01N 33/00* | (2006.01) | |
| *H01Q 1/22* | (2006.01) | |
| *H05K 1/11* | (2006.01) | |
| *H01L 29/06* | (2006.01) | |
| *B82Y 40/00* | (2011.01) | |

(52) U.S. Cl.
CPC ......... *H05K 1/0243* (2013.01); *B29C 64/112* (2017.08); *G01N 33/0009* (2013.01); *H01Q 1/2283* (2013.01); *H05K 1/0284* (2013.01); *H05K 1/118* (2013.01); *H05K 3/125* (2013.01); *B82Y 40/00* (2013.01); *H01L 29/0669* (2013.01)

(58) Field of Classification Search
CPC .... H05K 1/0243; H05K 1/0284; H05K 1/118; H01Q 1/2283
See application file for complete search history.

(56) References Cited

U.S. PATENT DOCUMENTS

| | | | | |
|---|---|---|---|---|
| 2007/0222010 | A1* | 9/2007 | Chou | G06V 40/1329 257/415 |
| 2010/0078806 | A1* | 4/2010 | Chakrapani | H01L 23/373 257/E23.101 |
| 2014/0273259 | A1* | 9/2014 | Friedman | B82Y 15/00 436/112 |

(Continued)

*Primary Examiner* — Hoa C Nguyen
(74) *Attorney, Agent, or Firm* — Christopher O. Edwards; Bryan A. Geurts; Helen M. Galus (57) ABSTRACT

The present invention relates to a multi-functional platform, including: a printed circuit board (PCB) having a single chip integrated thereon; wherein the single chip includes a substrate having an environmental system disposed thereon, the environmental system including a plurality of three-dimensional (3D) printed, patterned and multi-layered nanostructures disposed on the substrate. The nanostructures include an on-chip heater, a power source, a wireless communication module, and a plurality of sensors, the sensors including at least one of a gas sensor, a pressure sensor, or a temperature sensor, each of which is directly deposited on the substrate and printed with a plurality of nanomaterials. The 3D patterned nanostructures use functionalized nanomaterials, which are patterned by a template using one of directed assembly or nano-offset printing, to deposit the nanostructures directly on the substrate of the single chip.

23 Claims, 2 Drawing Sheets

(56) References Cited

U.S. PATENT DOCUMENTS

| | | | |
|---|---|---|---|
| 2014/0318967 A1* | 10/2014 | Busnaina | G03F 7/0002 |
| | | | 204/485 |
| 2016/0072007 A1* | 3/2016 | Choi | H01L 33/0025 |
| | | | 315/291 |
| 2017/0200760 A1* | 7/2017 | Zhang | H01L 27/1462 |
| 2017/0330010 A1* | 11/2017 | Khalid | G01R 27/2605 |
| 2018/0045698 A1* | 2/2018 | Sultana | G01N 27/127 |
| 2018/0059080 A1* | 3/2018 | Jun | G01N 33/0013 |
| 2018/0136537 A1* | 5/2018 | Kim | G02F 1/292 |
| 2019/0131196 A1* | 5/2019 | Cook | H01L 23/28 |
| 2020/0098560 A1 | 3/2020 | Petkov et al. | |

* cited by examiner

MULTI-FUNCTIONAL NANOMATERIAL SENSOR PLATFORM

ORIGIN OF THE INVENTION

The invention described herein was at least in-part made by an employee of the United States Government and may be manufactured or used by or for the Government of the United States of America for governmental purposes without the payment of any royalties thereon or therefor.

BACKGROUND OF THE INVENTION

1. Field of the Invention

The present invention relates to a lightweight, small, and low power, in situ multifunctional sensor platform created by printing a suite of environmental sensors made of nanomaterials, and other components, directly on the substrate of a chip.

2. Description of the Related Art

Currently, sensors and electronics are printed onto separate chips and then electronically interconnected to outputs as well as to each other. Although nanomaterials have been used in sensors in the lab to demonstrate superior device performance and miniaturization, and also used in a variety of other applications such as electronics, optics, energy harvesting and storage, and biotechnology, nanomaterial-based devices have challenges including scalability, and tedious manual fabrication processes, leading to low yield and poor reproducibility. More importantly, the integration of different components has not been fully addressed prior to this work. Consequently, there have not been any nanomaterial-based multifunctional sensor product for commercial or space applications to date.

Some of the challenges discussed above have been addressed by various techniques such as nanomaterial fluidic assembly process using capillary force, and electro-hydrodynamic jet printing. However, although these processes have shown precision assembly with high resolution at the micro and nanoscale, each has serious scalability and throughput shortcomings, in addition to alignment issues required to fabricate multilayered structures with different materials.

Furthermore, current printing methods produce sensors on a micron scale. The resulting suite of separate sensors and electronics forms a large package prone to failure via its fragile interconnects.

In addition, mass interference makes it difficult to separate various gases etc., such as hydrogen ($H_2$) and hydrogen sulfide ($H_2S$), and compounds like methane ($CH_4$), ammonia ($NH_3$), and water ($H_2O$) (three of the key species for the origin of life, using mass spectrometers. The detection limit of the state-of-the-art mass spectrometer flown to Mars on Curiosity for these gases and compounds is in the parts per million (ppm).

Further, mass spectrometers also have a comparatively large resource footprint. Mass Spectrometry (MS) is one of the state-of-the-art technologies for in silt trace gas detection that has been successfully flown on many missions. However, it uses mass to charge (m/z) ratio to identify gas species, and many trace gases of interest (e.g., $CH_4$ and $NH_3$; $NH_3$ and $H_2O$; nitrogen ($N_2$) and carbon monoxide (CO)) have overlapping m/z ratios, making it difficult to distinguish from one another using MS. In addition, the large size and high power requirements make MS difficult to use in low budget missions.

Accordingly, since the cost of space missions depend directly on the size, weight, power and complexity of payloads, a multi-functional sensor platform which can provide all the features to detect gases and compounds, in a small, lightweight package of sufficient power, is needed.

SUMMARY OF THE INVENTION

The present invention relates to a lightweight, small, and low power, in situ, autonomous multifunctional sensor platform created by printing a highly sensitive, stable, environmental sensor system made of nanomaterials, and other components, directly on the substrate of a chip.

In one embodiment, the present invention includes a single, printed chip having an assortment of directly deposited sensors with nanometer-scaled materials and associated electronics for onboard computation, on-chip heaters, power source and wireless communication module, packaged in a self-contained unit, by leveraging an innovative three-dimensional (3-D) micro- and nano-scale printing technique, which results in an instrument with reduced weight, reduced size and increased robustness.

In one embodiment, the 3-D micro- and nano-scale additive manufacturing printing technique allows the printing of nanostructures, as well as a variety of nanomaterials including carbon nanotube (CNT), graphene, molybdenum disulfide, and metal leads on either rigid or flexible substrates. The ability to print the sensor systems, and partial circuitry of the wireless communication module directly on the same daughterboard, which is then packaged with a Printed Circuit Board (PCB) including electronics, power source and the rest of the communication circuitry, advantageously eliminates the need to integrate individually fabricated components. This makes the packaging significantly more robust and reduces the resource footprint of the sensor platform. The sensors and components are integrated to form a multifunctional sensor platform In one embodiment, the environmental sensor system includes nanomaterial-based gas, temperature and pressure sensors, including for example, hydrogen ($H_2$), hydrogen sulfide ($H_2S$), methane ($CH_4$), ammonia ($NH_3$), and water ($H_2O$). In one embodiment, microheaters are also present, in addition to an antenna for wireless communication. In one embodiment, the sensor suite is then integrated to radiation hard readout electronics.

The directed assembly-based printing processes of the present invention are specifically developed to be scalable, high-throughput, automated, and achieve precise alignment and repeatable control over the printing of various structures, interconnects, and circuits on rigid or compliant substrates using ordered arrays and networks of metallic, semiconducting, or insulating nanoparticles, conductive polymers.

The realization of a low resource, yet high performance, autonomous multifunctional sensor platform will greatly benefit a broad range of space missions, for example, as well as science applications, medical applications, and more.

In one embodiment, a multi-functional platform, includes: a printed circuit board (PCB) including a single chip; wherein the single chip includes a substrate having an environmental system disposed thereon; wherein the environmental system includes: a plurality of three-dimensional (3D) printed, patterned and multi-layered nanostructures disposed on the substrate; and wherein the plurality of nanostructures includes a plurality of nanomaterials.

In one embodiment, the plurality of nanostructures includes a plurality of sensors, each of the plurality of sensors which are directly deposited on the substrate and printed with the plurality of nanomaterials; and wherein the plurality of sensors includes at least one of a gas sensor, a pressure sensor, or a temperature sensor.

In one embodiment, the plurality of nanostructures includes an on-chip heater, a power source, and a wireless communication module.

In one embodiment, the wireless communication module includes an antenna.

In one embodiment, the plurality of nanomaterials includes at least one of carbon nanotube (CNT), graphene, molybdenum disulfide, or metal leads, disposed on the substrate.

In one embodiment, the substrate is one of rigid or flexible.

In one embodiment, the plurality of nanomaterials are made of a radiation hardened material.

In one embodiment, the plurality of sensors includes multiple, different sensors, each functionalized with at least one different functional group; and wherein each of the multiple, different sensors have a same printed geometry, depending on the functional group attached to the plurality of nanomaterials from which the multiple, different sensors are printed.

In one embodiment, the plurality of sensors are parallel printed, with each of the plurality of sensors being functionalized at a same time.

In one embodiment, each of the multiple, different sensors have a different attached functional group, and the multiple, different sensors are disposed in an array which includes an electronic nose.

In one embodiment, the plurality of sensors and the wireless communication module are disposed directly on the single chip which is then integrated and packaged with the PCB.

In one embodiment, each gas sensor is configured to detect at least one single gas, such that gases with mass interference can be distinguished without a mass spectrometer.

In one embodiment, each gas sensor can detect at least one of hydrogen ($H_2$), hydrogen sulfide ($H_2S$), methane ($CH_4$), ammonia ($NH_3$) or water ($H_2O$).

In one embodiment, after the plurality of sensors are 3D printed, each of the plurality of sensors are functionalized with one of metal or metal oxide nanoparticles, or polyaniline, porous ceramic nanoparticles (NP), platinum NP, polyaniline film, or tin oxide NP.

In one embodiment, the plurality of sensors can detect at least one single gas in one of a parts per million, a parts per billion, or a parts per trillion, concentration.

In one embodiment, the pressure sensor is made of suspended molybdenum disulfide ($MoS_2$)-based Field-Effect Transistors (FETs).

In one embodiment, the pressure sensor is printed directly on the substrate with unfunctionalized multiwall carbon nanotubes (CNT) that form a network which is sensitive to pressure.

In one embodiment, the temperature sensor includes a thermistor printed with platinum nanoparticles.

In one embodiment, the temperature sensor has an accuracy of 1° C.

In one embodiment, the on-chip heater is a microheater printed directly on the substrate using conductive nanomaterials including one of silver nanoparticles, platinum nanoparticles or carbon-based ink.

In one embodiment, the microheater is capable of reaching temperatures up to 300° C.

In one embodiment, the antenna is printed using one of carbon nanotube (CNT), silver or gold.

In one embodiment, the platform further includes: a configurable field programmable gate array (FPGA) which processes data from the chip to an RF transceiver, which forwards the data to the antenna for transmission.

In one embodiment, a method of manufacturing a multifunctional platform, includes: providing a printed circuit board (PCB); providing a single chip having a substrate, the single chip which is integrated on the PCB; providing at least one template which is patterned using microelectronic processing; functionalizing a plurality of nanomaterials; forming a plurality of three dimensional (3D) patterned multi-layered nanostructures using the functionalized plurality of nanomaterials, with the template; using one of directed assembly or nano-offset printing to deposit the plurality of 3D patterned nanostructures formed from the plurality of nanomaterials directly on the substrate of the single chip, and integrating the single chip with the PCB.

In one embodiment, the plurality of patterned nanostructures includes one of a plurality of sensors, each of the plurality of sensors which are directly deposited on the substrate and printed with the plurality of nanomaterials; and wherein the plurality of sensors includes at least one of a gas sensor, a pressure sensor, or a temperature sensor.

In one embodiment, the method further includes: attracting the plurality of nanomaterials to the plurality of patterned nanostructures using electrophoresis.

In one embodiment, fluidic assembly is used to deposit the plurality of nanomaterials directly to the substrate.

In one embodiment, the nano-offset printing further includes: individually forming the plurality of nanostructures by precise patterns on the template.

In one embodiment, the integrating step is a pressing step.

In one embodiment, the plurality of nanomaterials are functionalized prior to the nano-offset printing process.

In one embodiment, the method further includes: integrally depositing directly on the single chip, a plurality of electrical components, including at least one of a microheater or a wireless communication module.

In one embodiment, the method further includes automating the nano-offset printing.

In one embodiment, the at least one template is used to create the plurality of sensors, the plurality of sensors which include multiple, different sensors, each functionalized with at least one different functional group.

In one embodiment, each template is aligned so that a bridge spans a distance in-between two electrodes of a plurality of electrodes on the chip, and a material for the bridge includes a plurality of nanomaterials including at least one of Single Wall Carbon Nanotubes (SWCNT), Multi-Wall Carbon Nanotubes (MWCNT), Molybdenum Disulfide ($MoS_2$), Tungsten Disulfide ($WS_2$) or graphene.

In one embodiment, the method further includes: controlling an angle of the plurality of nanomaterials that form the bridge between the two electrodes of the chip, such that an alignment results in a consistent number and geometry of nanomaterial bridges present between the two electrodes and produces consistent electrical properties across production of all the plurality of sensors.

In one embodiment, the plurality of nanomaterials for the bridge and the plurality of electrodes are each manufactured separately using one of a template for each, or by direct assembly; and each template of the bridge and the plurality of electrodes is loaded with the plurality of nanomaterials that form the bridge, and then pressed onto the substrate, imprinting the loaded plurality of nanomaterials on the substrate.

In one embodiment, the plurality of nanomaterials that form the bridge includes a deposited functional group, each functional group which is associated with a response; and wherein the functional group and the plurality of nanomaterials which form the bridge include at least one of Palladium (Pd), Platinum (PT), Ruthenium (Ru), Silver (Ag), or Tin Oxide (SnO2).

In one embodiment, the plurality of nanomaterials which form the bridge is functionalized via one of physical vapor deposition, electron beam evaporation or solution phase functionalization.

In one embodiment, the integration of the single chip with the PCB is performed by one of wire bonding, bump bonding, aerosol jet printing, or offset printing techniques.

In one embodiment, after the plurality of sensors are 3D printed, the plurality of sensors are functionalized with one of metal or metal oxide nanoparticles, or polyaniline, porous ceramic nanoparticles (NP), platinum NP, polyaniline film, or tin oxide NP.

In one embodiment, the pressure sensor is printed directly on the substrate with unfunctionalized multiwall carbon nanotubes (CNT) that form a network which is sensitive to pressure.

In one embodiment, the temperature sensor is printed using one of offset printing or aerosol jet printing, using a conductive nanomaterial including one of silver nanoparticles, platinum nanoparticles or carbon-based ink.

In one embodiment, the on-chip heater is a microheater printed directly on the substrate using one of offset printing or aerosol jet printing, using conductive nanomaterials including one of silver nanoparticles, platinum nanoparticles or carbon-based ink.

In one embodiment, the antenna is printed using one of carbon nanotube (CNT), silver or gold, using one of offset printing, aerosol jet printing or by direct assembly.

In one embodiment, the wireless communication module is achieved by printing the antenna and other Radio Frequency (RF) passive components and interconnects on the single chip, and surface mounting electronics including a RF transceiver, on the PCB.

Thus, has been outlined, some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The description of the drawings includes exemplary embodiments of the disclosure and are not to be considered as limiting in scope.

DESCRIPTION OF THE INVENTION

The present invention relates to a lightweight, small, and low power, in situ, autonomous multifunctional sensor platform created by printing a highly sensitive, stable, environmental sensor system made of nanomaterials, and other components, directly on the substrate.

In one embodiment, the present invention includes a single chip 100 (see FIG. 1) on a Printed Circuit Board (PCB) 101 having an assortment of directly deposited sensors of an environmental sensor system, each printed with nanometer-scaled materials, for example (e.g., gas sensor 102, pressure sensor 103, temperature sensor 104, etc.), and associated electronics for onboard computation, on-chip heaters (e.g., micro-heater 105), power source and wireless communication module (e.g., antenna structure 106), packaged in a self-contained unit, by leveraging an innovative three-dimensional (3-D) micro- and nano-scale printing technique, which results in an instrument 100 with reduced weight, reduced size, reduced power and increased robustness.

Figure 1:
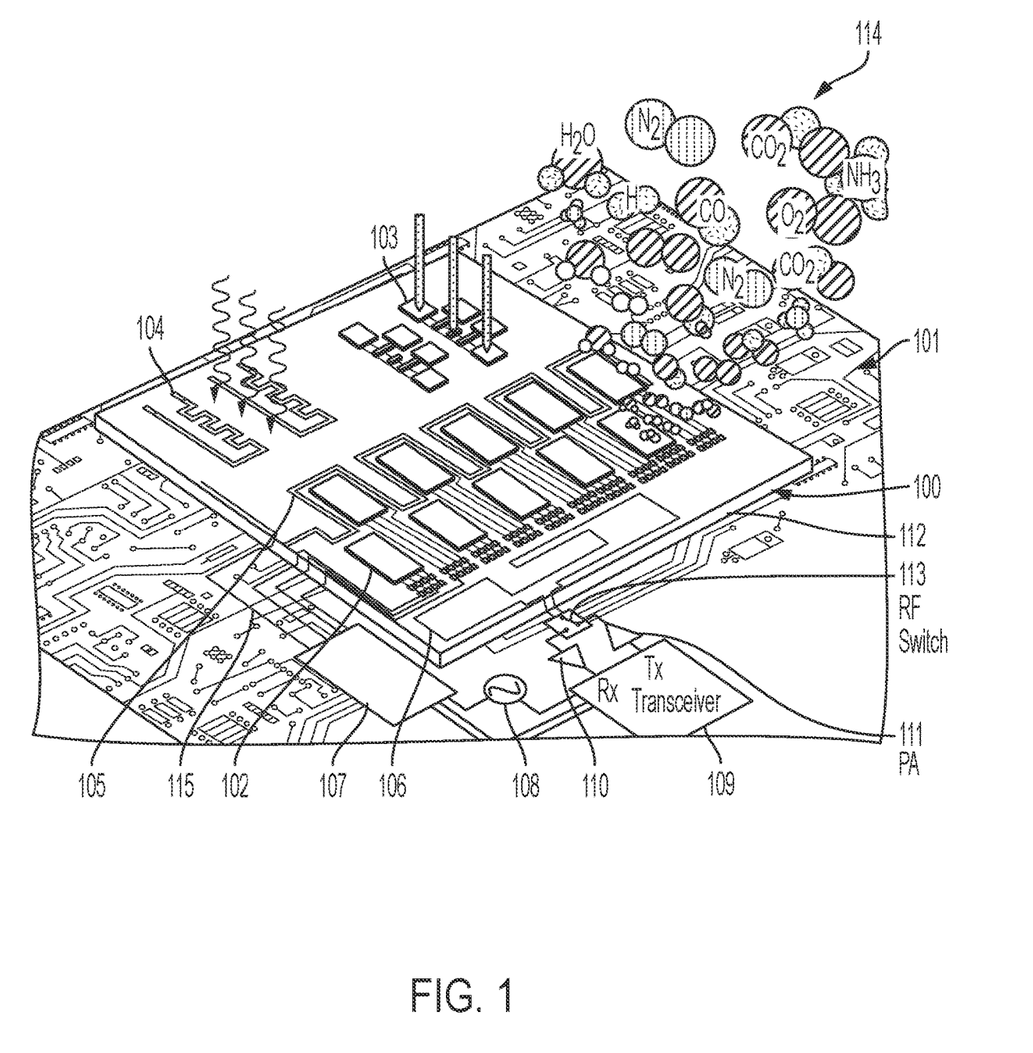
FIG. 1 is perspective drawing of a multi-functional sensor platform showing a suite of environmental sensors and other components, according to one embodiment consistent with the present invention.

In one embodiment, the 3-D micro- and nano-scale additive manufacturing printing technique allows the printing of patterned nanostructures (i.e., sensors, antenna etc.), as well as a variety of nanomaterials including carbon nanotube (CNT), graphene, molybdenum disulfide, and metal leads 115 on either rigid or flexible substrates 112. In one embodiment, electrophoresis is used to attract the nanomaterials to the patterned features. In another embodiment, fluidic assembly is used to deposit the nanomaterials directly to the substrate.

In one embodiment, the nanomaterials used for the sensors (e.g., temperature sensors 104) show excellent properties. For example, the nanomaterials are highly sensitive (i.e., parts per billion) at room temperature, they have a high surface-to-volume ratio, superior electrical properties, and are low resource (i.e., small, light, low power). In one embodiment, the nanomaterials are made of a radiation hardened material.

In one embodiment, the directed assembly technique of the single integrated, non-etched chip 100 of the present invention is to reproducibly print multilayer structures with different materials onto a single substrate 112, which offers a unique solution to the fabrication, integration and packaging challenges of the multifunctional sensor platform 101. In one embodiment, the directed assembly technique utilizes reusable templates to print high resolution features over a large area in a short period of time.

More specifically, in one embodiment, nano-offset printing is used in chip 100 manufacturing, wherein the elements are individually formed (for example, via precise patterns on a template (e.g., Damascene template) using standard microelectronic processing techniques), and then integrated together in a pressing step, or the elements are assembled directly on the substrate 112 using fluidic assembly techniques. In one embodiment, the present invention provides a novel technique in the offset printing process by manipulating the printed material (e.g., CNT) before it enters the offset printing process.

In one exemplary embodiment of a manipulation of the printed material (e.g., CNT), is the functionalization of the carbon nanotubes and other base sensors (e.g., gas sensor 102) materials. One advantage of manipulating the material prior to the offset printing process is the ability to use the same template for multiple, different sensors (e.g., gas sensors 102), each functionalized with different functional groups 102, for example.

For example, one single template can produce many different gas sensors 102 with each sensor 102 having the same printed geometry, depending on the functional group attached to a carbon nanotube. Additionally, this enables parallel printing of these sensors 102 with each sensor 102 being functionalized at the same time. This parallel printing simplifies the production of an electronic nose 200 (see FIG. 2) that comprises multiple base gas sensors 102, each with a different attached functional group.

Prior to the novel technique of the present invention, nanomaterial-based sensors suffered from either random deposition, or variations induced by manual microfabrication processes. This random distribution and variation affect the performance and reproducibility of the sensors. Prior nanomaterial-based sensors did not control for alignment and positional of nanomaterials spanning between the electrodes. The resultant sensor could have none or many different pieces of a nanomaterial that form bridges connecting the two electrodes. Furthermore, each nanomaterial bridge could be composed of a different amount of nanomaterial.

In contrast, the present invention controls the angle of the deposited nanomaterials that form the bridge between the electrodes from 0 to 90 degrees. This alignment results in the consistent number and geometry of nanomaterial bridges to be present between the electrodes and produces consistent electrical properties across all sensor, i.e., gas sensor 102, production.

In one embodiment, the gas sensors 102, for example, include electrodes and bridging material which defines a span whose ends contact the electrodes. Non-limiting examples of bridging material include Single Wall Carbon Nanotubes (SWCNT), Multi-Wall Carbon Nanotubes (MWCNT), Molybdenum Disulfide ($MoS_2$), Tungsten Disulfide ($WS_2$) and graphene. In one embodiment, the sensor's (i.e., gas sensor 102) bridging components and electrodes each are manufactured separately using their own template or using direct assembly. In one embodiment, each template is loaded with their perspective material and then pressed onto a final substrate 112, imprinting the loaded material on the final substrate 112. In one embodiment, the templates are aligned so that the bridging material spans the distance in between the two electrodes.

In one embodiment, the bridging material may include a deposited functional group. Non-limiting examples of functional groups and bridging material are Palladium (Pd), Platinum (PT), Ruthenium (Ru), Silver (Ag), and Tin Oxide (SnO2). In one embodiment, each functional group is associated with a response. In one embodiment, the bridge material may be functionalized via physical vapor deposition, electron beam evaporation or solution phase functionalization.

In one embodiment, the present invention allows multiple layers to be printed, each in a few minutes, to create the final device 100 at a cost 10 times to 100 times less than conventional fabrication. Each template of the present invention can be used thousands of times, and can print features down to 20 nm, and can print 0, 1- and 2-D materials. The present process can print 1000 times faster than typical 3D printing, and a 1000-times smaller than ink-jet printing. The automated printing eliminates variation that results from manual manipulation or traditional fabrication techniques for nanomaterial-based devices. The automated printing not only increases reproducibility of nanomaterial-based devices, but also provides higher yield, high throughput, faster development time, precision alignment, and development of multilayer structures which are advantageous over existing systems.

In the present invention, the ability to 3D print the sensor systems (e.g., gas sensor 102, pressure sensor 103, temperature sensor 104 systems), and all the interconnects, and partial circuitry of the wireless communication module 106, directly on the same chip or daughterboard 100, which is then integrated and packaged with a Printed Circuit Board (PCB) 101 by wire bonding or bump bonding, aerosol jet printing or offset printing techniques, including electronics for onboard processing, power source, and the rest of the communication circuitry, advantageously eliminates the need to integrate individually fabricated components, with multiple sensors and electronic components each inhabiting their own individual chip 100, requiring further connections to each other or to front-end electronics.

As described above, in one embodiment, the environmental sensor system of the multi-sensor chip 100 includes, for example, nanomaterial-based gas sensors 102, pressure sensors 103 and temperature sensors 104, wherein the multiple gas sensors 102 are included in compact form, each of which has been designed to detect at least one single gas. In one embodiment, the species are detected by the electrochemical interactions with the sensor material. As a result, gases with mass interference can be distinguished by the multifunctional sensor platform of the present invention and not with a mass spectrometer This allows the measurement of individual gases that are difficult to measure with a mass spectrometer in bulk due to mass interference.

In one embodiment, non-limiting examples of the nanomaterial-based gas sensors 102 include, hydrogen ($H_2$), hydrogen sulfide ($H_2S$), methane ($CH_4$), ammonia ($NH_3$) or water ($H_2O$). However, one of ordinary skill in the art would know that the multifunctional platform can be customized for most other gases and volatiles, that can have applications in not just space science, but also process monitoring, medical diagnosis, etc.

In one embodiment, the gas sensors 102 are made using graphene and carbon nanotubes (CNT). After the sensors 102 are printed as described above, they are functionalized with, for example, metal or metal oxide nanoparticles, or with polyaniline, and for example, depending on the target gases, porous ceramic nanoparticles (NP), platinum NP, polyaniline film, or tin oxide NP. These functionalization methods are well established and have been demonstrated to induce selectivity for specific gases.

In one embodiment, the above gases include, but are not limited to, some of the key species for biological and geochemical processes, and since $H_2O$, $NH_3$ and $CH_4$ are difficult to distinguish with mass spectrometers due to mass interference issues, the present invention is an advancement over the present technology in environmental sensors.

In one embodiment of gas sensor 102 operation, for example, a target gas is adsorbed to the bridge material. This adsorption changes the electrical properties of the bridging materials. The bridging material acts as a chemi-resistive sensor or a field effect transistor (FET). The functional groups incorporated onto the bridging material affect the extent of adsorption of a specific analyte. Therefore, the incorporation of a functional group can change the adsorption or charge transfer of target species to the sensor 102 and result in a specific change in electrical properties. Accordingly, the sensors 102 of the present invention can detect a gas in various concentrations, including but not limited to, parts per million, parts per billion and parts per trillion concentration.

Figure 2:
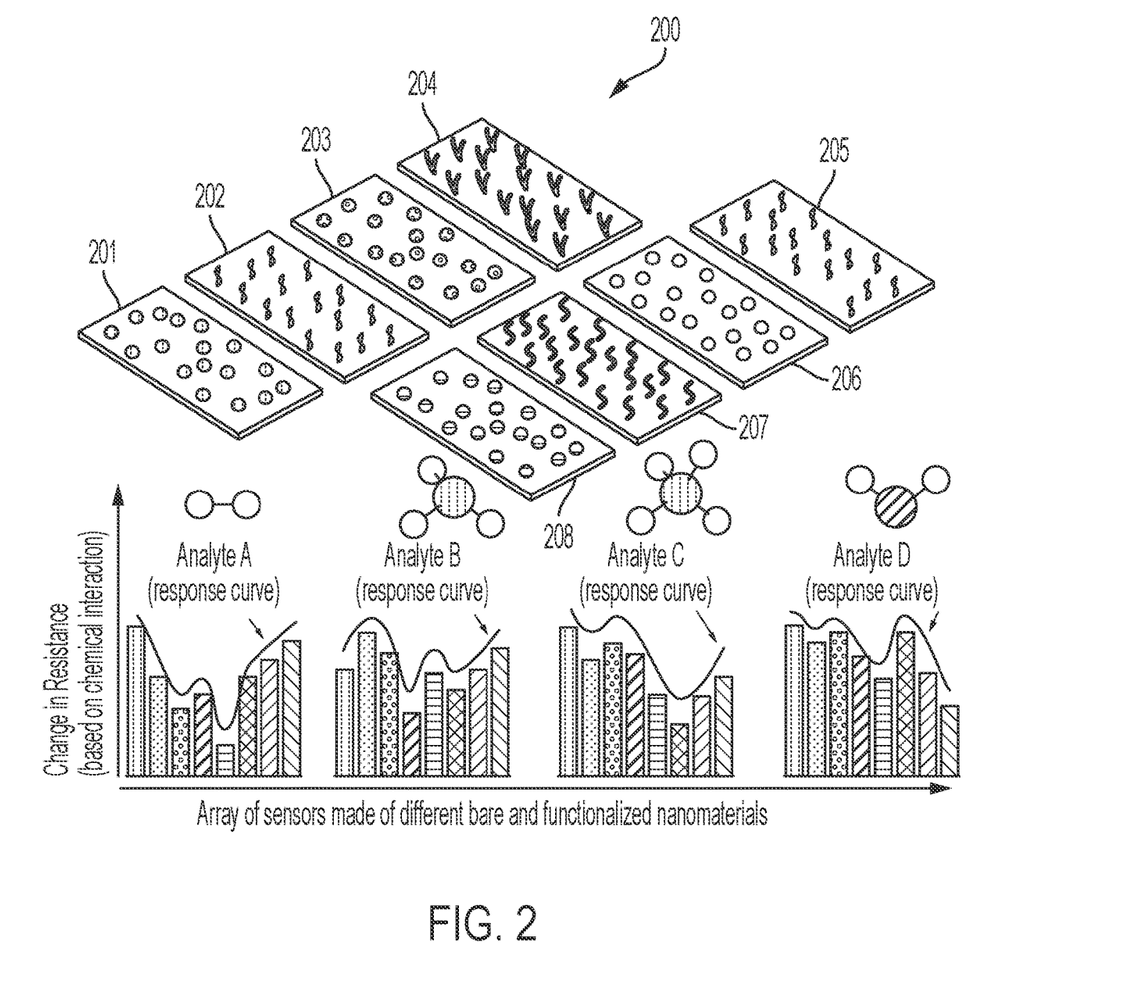
FIG. 2 is a perspective view of a sensor array made of different and functionalized nanomaterials, with a plurality of sensors which detect a plurality of analytes, and the corresponding graphs thereof showing a change in resistance based on chemical interaction, according to one embodiment consistent with the present invention.

In one embodiment, the gas sensors 102 of the present invention can be used to produce an electronic nose 200 (see FIG. 2). In one embodiment, the electronic nose 200 of the present invention is composed of a sensor array 200, with each sensor 201-208 having a different incorporated functional group. In one embodiment, when a target analyte (analyte A through analyte D) is adsorbed by the sensor array 200, it changes the electrical properties of each sensor 201-208 in that array 200. However, the analyte may change each individual sensor 201-208 by a different amount. For example, in an eight-sensor array 200 as shown in FIG. 2, an analyte might drastically change the electrical properties of one of the sensors (e.g., sensor 201) while not affecting the electrical properties of a different sensor (e.g., sensor 205).

Gases interact with different sensor material and different functional groups in a certain manner based on the chemical affinity and from the interaction, the gases can be characterized. Gases may respond to a functional group with varying high or low chemical interactions resulting in high or low changes in resistance. These resistance changes over multiple different sensors 201-208 of the present invention, can produce a response curve that can be analyzed to characterize the specific gas (see FIG. 2). This enables the measurement of analytes (e.g., analyte A through analyte D) where the gas sensors 102 are not specifically functionalized to measure those gases.

In one embodiment, the environmental sensor system of the present invention includes pressure sensors 103 made of suspended molybdenum disulfide ($MoS_2$)-based Field-Effect Transistors (FETs), for example. In one embodiment, silicon oxide ($SiO_2$) is etched to make trenches on which $MoS_2$ is transferred to make suspended channels, with air trapped beneath it. As the ambient air pressure changes, $MoS_2$ is strained, and the inherent piezoelectricity of $MoS_2$ results in a measurable response.

In one embodiment, the pressure sensors 103 can be printed directly on the same sensor substrate 112 using the printing technique including printing a nanomaterial on a trench where the nanomaterial acts as a membrane, using offset printing or direct assembly. It is printed with unfunctionalized multiwall carbon nanotubes (CNT) that form a network which is sensitive to pressure. In another embodiment, the nanomaterial can be printed on a flat substrate. In one embodiment, pressure changes apply stress on the CNT network, which alters the connectivity of the nanotubes in the network, which increases the resistance. In one embodiment, the pressure sensor 103 measures the change in resistance, and thus, calculates the change in pressure.

In one embodiment, the environmental sensor system includes a temperature sensor 104, which includes, for example, a simple thermistor printed with platinum nanoparticles. Thermistors are a type of resistor that function as a heating element and thermo-sensitive device. Heat is generated by an applied voltage and current, and the resistance changes with the change of temperature. In one embodiment, the temperature sensor 104 measures a change in resistance and thus, calculates a change in temperature. In one embodiment, the change in resistance is carefully calibrated with respect to temperature and an accuracy of 1° C. has been achieved.

In one embodiment, the temperature sensors 104 can be printed using the above-described printing procedure, including but not limited to offset printing or aerosol jet printing techniques. In one embodiment, the temperature sensor 104 is printed with a conductive nanomaterial, such as, for example, silver nanoparticles, platinum nanoparticles or carbon-based ink.

In one embodiment, a microheater 105 is printed directly on the sensor substrate 112 using printing techniques, including but not limited to offset printing or aerosol jet printing techniques. The microheater 105 is printed with conductive nanomaterials, such as silver nanoparticles, platinum nanoparticles or carbon-based ink, for example. Microheaters are used for temperature control. A microheater is essentially a resistance heater and, as such, it operates by passing an electric current across the filament to generate heat. In one embodiment, the microheaters 105 are located close to the gas sensors 102 in order to efficiently heat the gas sensors. In one embodiment, the micro-heaters 105 of the present invention are capable of reaching temperatures up to 300 degrees Centigrade.

In one embodiment, an antenna structure 106 is included on the multi-sensor chip 100. The printing technology of the present invention, as described above, is also used to make carbon nanotube (CNT) antennas 106, for example. However, the antennas can be printed with any suitable conductive material, such as silver or gold. For example, the antenna structure 106 is printed on to the sensor chip 100 directly using printing techniques, including but not limited to offset printing, aerosol jet printing or direct assembly techniques. The small dimension and high permittivity of the nanomaterial enables miniaturization, and much like in a cell phone where the antenna is integrated using all available space including the chassis and ground plane, a planar variation of a patch antenna has been developed for the present invention, that optimizes antenna efficiency and gain.

In one embodiment, the wireless communication module is realized by printing the Radio Frequency (RF) passive components: the antenna 106, microstrip transitions, and interconnects on the daughterboard 100; and surface mounting the remaining electronics (e.g., transceiver 109) on the main PCB 101 to make up a full duplex communication system.

In one embodiment, the wireless communication module design of the present invention has been conceived with agile technology in mind to account for different scenarios and applications. The module design uses two integrated circuits (ICs), a configurable field programmable gate array (FPGA) 107 (i.e., from Microsemi) for data processing, and Analog Devices' highly integrated and configurable radio frequency (RF) transceiver 109 which connects to the antenna structure 106 via an RF switch 113 and power amplifier (PA) 111 and low noise amplifier (LNA) 110. Oscillator 108 forwards the data processed from the FPGA to the antenna for data transmission.

The present invention provides tighter integration and radiation hardness, and the electric and dielectric properties of CNT and graphene allows for a wireless communication architecture designed for configurability across multiple frequency bands (S-band and X-band) with a digital radio frequency (RF) conversion approach, enabling the use of sensors in a wide variety of applications. In one embodiment, the nanomaterial-based antenna structure 106 for RF/microwave applications can receive sensor data via interconnects from the temperature sensors 104, pressure sensors 103, and gas sensors 102, and transmit this data with the antenna 106, as well as receive communication commands.

In one embodiment, the gas sensors 102, temperature sensors 104, pressure sensors 103, microheaters 105 and wireless antenna 106 are all interconnected to a readout (not shown). In one embodiment, the interconnections may also be printed with offset printing, direct assembly or aerosol jet printing techniques, and therefore, are integrated into the final chip 100.

In one embodiment, the readout is a custom card that can read a plurality of sensors, for example, 10 gas sensors 102, two pressure sensors 103, and two temperature sensors 104, simultaneously. In one embodiment, the readout of the present invention can measure 0.01% resistance change. In one embodiment, the readout can trigger the micro heaters 105 according to the measurements from the other sensors 102-104. In one embodiment, the electronic components and sensors on the platform 101 of the present invention may have features that can be printed down to as low as 10 nm width and are able to scale up to any larger size design requirements.

In one embodiment, the multi-sensor platform of the present invention may include 10 different gas sensors 102, as well as two pressure sensors 103, two temperature sensors 104, with microheaters 105, and a wireless module with antenna structure 106, all on a 1 cm×1 cm chip 100, disposed on a PCB of approximately 3 cm square, for example. However, one of ordinary skill in the art would know that the types and numbers of sensors can be varied depending on user requirements.

In one embodiment, a solar array (not shown) composed of high efficiency gallium arsenide solar cells coupled to a lithium-ion battery pack is used as a power source for the present invention. The charging of the battery from the solar array is regulated, preventing overcharging and inconsistent solar energy issues, while delivering the appropriate loads to the senor array, transmitter, avionics, and operational heaters. The present invention incorporates radiation tolerant elements appropriate for space or planets without protective magnetospheres. In one embodiment, for planetary missions where fouling of the solar cell surface is an issue, the array will incorporate an electrodynamic dust shield (not shown) to clean the solar cells.

In sum, the innovation of the present invention incorporates gas sensors, temperature sensors and pressure sensors, all of which may be mixed and matched, and integrally deposited on a single chip. The interconnects of the present invention serve as an integral connection in-between sensors, electrical components, and electrical outputs. In one embodiment, the multi-sensor chip of the present invention incorporates multiple gas sensors in a compact form, each of which has been designed to detect at least a single gas. This allows the measurement of individual gases that are difficult to measure, or difficult to distinguish due to mass interference issues, using a mass spectrometer.

In one embodiment, the electrical components (e.g., micro-heaters, electrical interconnections and wireless communication electronics, like S and X band antennas) may also be integrally deposited directly on to the same chip as the sensors. In one embodiment, each sensor and electrical components may be composed of different materials.

The novel 3-D printing process of the present invention is compact and fully automated allowing for manufacturing to occur on-site. In one embodiment, the packaging of the present invention is significantly more robust and reduces the resource footprint of the sensor platforms. This allows an instrument's performance to be remotely analyzed and new sensors manufactured in space according to any new specification or situation. The integral layout of the sensors and electrical components allow a simultaneous readout from each sensor.

The advantages of the multi-sensor chip of the present invention are its low weight, compact packaging, low power requirements, and increased robustness. The multi-sensor chip is small in size and weight due to its nanometer scale manufacturing process that tightly integrates all of its components on a single chip. Furthermore, the multi sensor chip exhibits radiation hardness and increased robustness due to all the integrally connected electronics. The nanomaterial-based components also contribute to its decreased power consumption.

Thus, the challenges associated with the traditional fabrication methods of nanomaterial-based devices, which have made it difficult to realize commercial applications, due to labor intensiveness, low yield, long development time, lack of reproducibility from sensor to sensor, and general lack of reliability, are removed. The present invention addresses these disadvantages.

For example, the directed assembly-based printing processes of the present invention are specifically directed to be scalable, high-throughput, automated, and achieve precise alignment and repeatable control over the printing of various structures, interconnects, and circuits on rigid or compliant substrates using ordered arrays and networks of metallic, semiconducting, or insulating nanoparticles, and conductive polymers.

The multifunctional sensor platform of the present invention represents a game changing capability of manufacturing and deploying sensors in places, and in quantities, not previously possible. For example, the cost of space missions depends directly on the size, weight, power of the instruments. Currently, the size, weight and power of the current temperature, pressure and gas sensor platform (~72,000 cm3, 40 kg, and up to 480 W for a mass spectrometer instrument that went on space vehicle Curiosity called "Sample Analysis at Mars" (SAM)) limit instrumentation to a single location. By radically reducing the cost, size, weight and power, multiple sensors can be deployed in multiple different locations at the same time. This further allows for a network of sensors to record temporal measurements at multiple locations, or to pinpoint the source of different gases or measure pressure and temperatures in a plurality of locations.

The present invention can provide critical, crosscutting, low resource breakthroughs applicable to many areas. For instance, planetary science can use it to detect gases that can help fingerprint various biological and abiotic processes on outer planets, moons such as Europa and Enceladus, comets, and asteroids. More specifically, the sensor platform of the present invention can be tailored to detect methane ($CH_4$), ammonia ($NH_3$) and other gases difficult to detect using Mass Spectrometry (MS) due to mass interference issues.

In addition, these small, low power sensors of the present invention can be employed to quickly pre-screen samples or monitor outgassing of samples during storage in case of sample return missions without adding much to the payload. Moreover, a network of autonomous sensor platforms of the present invention can be dropped off on Mars to study the seasonal and spatial variations of species of interest. For example, $CO_2$, $H_2O$, temperature and pressure, can be measured on Mars over several tens of kilometers in a potential landing zone to monitor local conditions with time, and the data can be wirelessly communicated to an orbiting spacecraft through the thin atmosphere. All of these missions will help us better understand the solar system and characterize in situ resources for future human missions to Mars.

In addition, a network of sensor platforms on the surface of the Moon or on lunar CubeSats will enable the study of water vapor cycle or to identify neutral atoms such as Atomic Oxygen (AO) without having to ionize them, as commonly done now, along with measuring the temperature and pressure.

In other advantages, the small size and low power requirements make the multifunctional sensor platform suitable for low-cost, small scale missions in lieu of some of the future large missions identified in the Decadal plans. Furthermore, a low resource autonomous multifunctional sensor platform could be critical for future human exploration missions, where detecting leaks of toxic gases in spacecraft is required to maintain crew health.

The present invention also has a simple operational method. The target species are detected by measuring electrical properties of the sensors, thus, avoiding the mass or spectral interferences encountered in traditional techniques. The ultralow resource footprint makes this multifunctional sensor platform suitable for missions with power and weight constraints and can characterize resources in planetary surfaces that can be leveraged for in situ resource utilization in human missions.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:
1. A multi-functional platform, comprising:
a printed circuit board (PCB) including a single chip;
wherein said single chip includes a substrate having an environmental system disposed thereon;
wherein said environmental system includes:
a plurality of three-dimensional (3D) printed, patterned and multi-layered nanostructures disposed on said substrate; and
wherein said plurality of nanostructures includes a plurality of nanomaterials.
2. The platform of claim 1, wherein said plurality of nanostructures includes a plurality of sensors, each of said plurality of sensors which are directly deposited on said substrate and printed with said plurality of nanomaterials; and
wherein said plurality of sensors includes at least one of a gas sensor, a pressure sensor, or a temperature sensor.
3. The platform of claim 2, wherein said plurality of nanostructures includes at least an on-chip heater, a power source, and a wireless communication module.
4. The platform of claim 3, wherein said wireless communication module includes an antenna.
5. The platform of claim 4, wherein said plurality of sensors and said wireless communication module are disposed directly on said single chip which is then integrated and packaged with said PCB.
6. The platform of claim 4, wherein said antenna is printed using one of carbon nanotube (CNT), silver or gold.
7. The platform of claim 4, further comprising:
a configurable field programmable gate array (FPGA) which processes data from said single chip and a RF transceiver and forwards said data to said antenna for transmission.
8. The platform of claim 3, wherein said on-chip heater is a microheater printed directly on said substrate using conductive nanomaterials including one of silver nanoparticles, platinum nanoparticles or carbon-based ink.
9. The platform of claim 8, wherein said microheater is capable of reaching temperatures up to 300° C.
10. The platform of claim 2, wherein said plurality of nanomaterials includes at least one of carbon nanotube (CNT), graphene, molybdenum disulfide, or metal leads, disposed on said substrate.
11. The platform of claim 10, wherein said plurality of nanomaterials are made of a radiation hardened material.
12. The platform of claim 2, wherein said plurality of sensors includes multiple, different sensors, each functionalized with at least one different functional group; and
wherein said each of said multiple, different sensors have a same printed geometry, depending on said functional group attached to said plurality of nanomaterials from which said multiple, different sensors are printed.
13. The platform of claim 12, wherein said plurality of sensors are parallel printed, with each of said plurality of sensors being functionalized at a same time.
14. The platform of claim 12, wherein each of said multiple, different sensors have a different attached functional group, and said multiple, different sensors are disposed in an array which comprises an electronic nose.
15. The platform of claim 12, wherein after said plurality of sensors are 3D printed, each of said plurality of sensors are functionalized with one of metal or metal oxide nanoparticles, or polyaniline, porous ceramic nanoparticles (NP), platinum NP, polyaniline film, or tin oxide NP.
16. The platform of claim 2, wherein each said gas sensor is configured to detect at least one single gas, such that gases with mass interference can be distinguished without a mass spectrometer.
17. The platform of claim 16, wherein each said gas sensor can detect at least one of hydrogen ($H_2$), hydrogen sulfide ($H_2S$), methane ($CH_4$), ammonia ($NH_3$) or water ($H_2O$).
18. The platform of claim 16, wherein said plurality of sensors can detect said at least one single gas in one of a parts per million, a parts per billion, or a parts per trillion, concentration.
19. The platform of claim 2, wherein said pressure sensor is made of suspended molybdenum disulfide ($MoS_2$)-based Field-Effect Transistors (FETs).
20. The platform of claim 2, wherein said pressure sensor is printed directly on said substrate with unfunctionalized multiwall carbon nanotubes (CNT) that form a network which is sensitive to pressure.

21. The platform of claim 2, wherein said temperature sensor includes a thermistor printed with platinum nanoparticles.

22. The platform of claim 21, wherein said temperature sensor has an accuracy of 1° C.

23. The platform of claim 1, wherein said substrate is one of rigid or flexible.

\* \* \* \* \*